(12) United States Patent
Mukai et al.

(10) Patent No.: US 8,998,872 B2
(45) Date of Patent: Apr. 7, 2015

(54) ABSORBENT ARTICLE

(75) Inventors: Hirotomo Mukai, Kagawa (JP);
Yoshihisa Watabe, Kagawa (JP)

(73) Assignee: Unicharm Corporation, Ehime (JP)

( * ) Notice: Subject to any disclaimer, the term of this patent is extended or adjusted under 35 U.S.C. 154(b) by 206 days.

(21) Appl. No.: 13/639,617

(22) PCT Filed: Apr. 7, 2011

(86) PCT No.: PCT/JP2011/058842
§ 371 (c)(1),
(2), (4) Date: Nov. 15, 2012

(87) PCT Pub. No.: WO2011/126088
PCT Pub. Date: Oct. 13, 2011

(65) Prior Publication Data
US 2013/0060219 A1    Mar. 7, 2013

(30) Foreign Application Priority Data
Apr. 7, 2010 (JP) ................................ 2010-088917

(51) Int. Cl.
*A61F 13/15* (2006.01)
*A61F 13/49* (2006.01)
*A61F 13/496* (2006.01)
*A61F 13/84* (2006.01)

(52) U.S. Cl.
CPC ..... *A61F 13/49058* (2013.01); *A61F 13/49009* (2013.01); *A61F 13/49011* (2013.01); *A61F 13/49017* (2013.01); *A61F 13/496* (2013.01); *A61F 2013/15121* (2013.01); *A61F 2013/49026* (2013.01); *A61F 2013/8497* (2013.01)

(58) Field of Classification Search
USPC ............ 604/385.24, 385.25, 385.26, 385.29, 604/385.3
See application file for complete search history.

(56) References Cited

U.S. PATENT DOCUMENTS

| 6,307,119 | B1 | 10/2001 | Cammarota et al. |
| 2002/0072728 | A1 * | 6/2002 | Shinohara et al. ....... 604/385.29 |
| 2005/0010188 | A1 | 1/2005 | Glaug et al. |

FOREIGN PATENT DOCUMENTS

| EP | 0456885 A1 | 11/1991 |
| EP | 1541098 A1 | 6/2005 |
| JP | 9084824 A | 3/1997 |

(Continued)

OTHER PUBLICATIONS

International Search Report corresponding to PCT/JP2011/058842, dated May 24, 2011.

(Continued)

*Primary Examiner* — Jacqueline F. Stephens
(74) *Attorney, Agent, or Firm* — Lowe Hauptman & Ham, LLP

(57) ABSTRACT

In a crotch region in the disclosed absorbent article, a waist elastic member provided in a front waist region, and waist elastic members provided in a rear waist region are arranged so as to not come into contact with each other, and a linear identification part is provided in either the front waist region or the rear waist region, in a manner such that in a first region wherein an absorbent main body is provided the identification part is only visible from the side of the absorbent article which is not in contact with the skin, and in a second region wherein the absorbent main body is not provided the identification part is visible from both the side of the absorbent article which is in contact with the skin and that which is not.

6 Claims, 13 Drawing Sheets

(56) References Cited

FOREIGN PATENT DOCUMENTS

| | | |
|---|---|---|
| JP | 10298801 A | 11/1998 |
| JP | 2003501209 A | 1/2003 |
| JP | 2005237768 A | 9/2005 |
| JP | 2008200410 A | 9/2008 |
| WO | 0076439 A2 | 12/2000 |
| WO | 2008/068646 A1 | 6/2008 |

OTHER PUBLICATIONS

Extended European Search Report issued Sep. 3, 2014, corresponding to European patent application No. 11765988.8.

* cited by examiner

FIG. 13
(a)
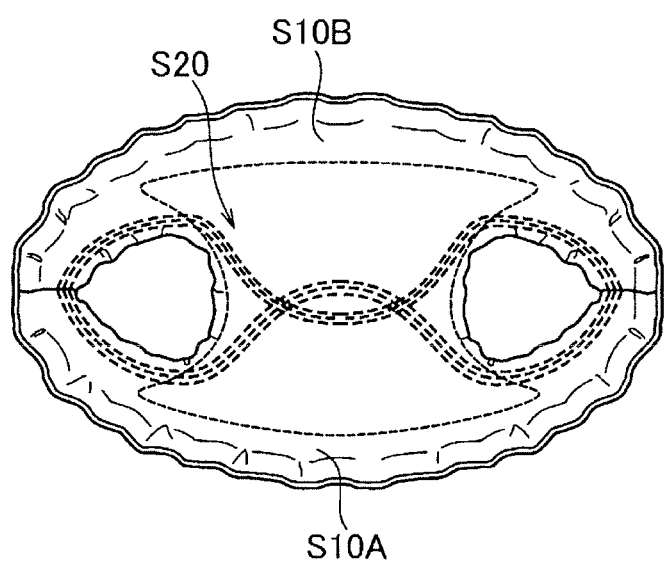
(b)
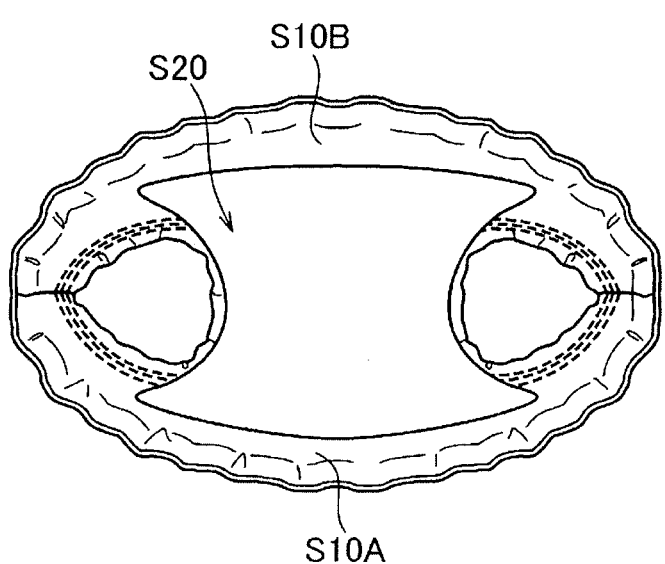

ABSORBENT ARTICLE

RELATED APPLICATIONS

The present application is a National Phase of International Application Number PCT/JP2011/058842, filed Apr. 7, 2011, and claims priority from Japanese Application Number 2010-088917, filed Apr. 7, 2010.

TECHNICAL FIELD

The present invention relates to an absorbent article.

BACKGROUND ART

Conventionally, there has been known an absorbent article which has a chassis containing a front waistline region, a rear waistline region, and a crotch region, and an absorber provided over the crotch region to the front waistline region and the rear waistline region.

Such a configuration of the absorbent article has been applied to both of an absorbent article for infants and an absorbent article for adults.

In these absorbent articles, the absorbent article for infants is often given such a design that is visibly recognizable from the outer surface (for example, see Patent Literature 1).

CITATION LIST

Patent Literature

Patent Literature 1: Japanese Patent Application Publication (Translation of PCT Application) No. 2003-501209

SUMMARY OF INVENTION

However, the applicants face the following problem as regard the aforementioned absorbent article.

In the absorbent article for adults with a configuration described above, it is often the case that the exterior surface of the absorbent article is not given any character images or the like, and in some cases, the chassis and the absorber have the same color.

Further, in a case of the absorbent article for adults, it is also assumed that a wearer wears the absorbent article again after taking it off once at bath time or the like.

Therefore, in a case of the absorbent article which has the chassis and absorber in the same color, it is difficult for the wearer to discriminate between the front side and the rear side. Therefore, when the absorbent article which was once taken off is worn again, this absorbent article is possibly worn inside out.

Further, in a case of the absorbent article in which elastic members for leg-hole gathers provided in a front waistline region S10A and elastic members for leg-hole gathers provided in a rear waistline region S10B are arranged so as to be in contact with each other in a crotch region S20, the feeling of comfort at the time of wearing is clearly different between a case as shown in FIG. 13(a) in which the absorbent article is worn in a normal state and a case as shown in FIG. 13(b) in which the absorbent article is worn inside out, so that a wearer can immediately notice the fact that he or she is wearing the absorbent article inside out.

On the other hand, in a case of the absorbent article in which the elastic members for the leg-hole gathers provided in the front waistline region S10A and the elastic members for the leg-hole gathers provided in the rear waistline region S10B are arranged so as not to be in contact with each other in the crotch region S20, there is a problem that a wearer cannot notice the fact that he or she is wearing the absorbent article inside out because the feeling of comfort at the time of wearing is not much different between a case in which the absorbent article is worn in a normal state and a case in which the absorbent article is worn inside out.

The present invention has been achieved in consideration of such circumstances, and an object thereof is to provide an absorbent article by which a wearer can easily discriminate between the front side and the rear side.

A first feature of the present invention is summarized as an absorbent article comprising: a chassis; and an absorber having a same color as the chassis; wherein the chassis has a front waistline region, a rear waistline region, and a crotch region intervened between the front waistline region and the rear waistline region;
the absorber is provided closer to a skin contact surface side of the absorbent article than the chassis, over the crotch region to the front waistline region and the rear waistline region; in the front waistline region and the rear waistline region, a plurality of waistline elastic members is provided along a width direction of the absorbent article; in the crotch region, the waistline elastic member provided in the front waistline region and the waistline elastic member provided in the rear waistline region are arranged so as not to come in contact with each other; in the front waistline region or the rear waistline region, an identifier of linear shape is provided so as to be visually recognizable from only a non-skin contact surface side of the absorbent article, in a first region which is provided with the absorber, and to be visually recognizable from both the non-skin contact surface side and the skin contact surface side of the absorbent article, in a second region which is not provided with the absorber; and the identifier is arranged over the first region and the second region.

As described above, according to the present invention, it is possible to provide an absorbent article by which a wearer can easily discriminate between the front side and the rear side.

BRIEF DESCRIPTION OF DRAWINGS

FIGS. 13(*a*) and 13(*b*) are views for illustrating a conventional absorbent article.

DESCRIPTION OF EMBODIMENTS

First Embodiment of Present Invention

Figure 1:
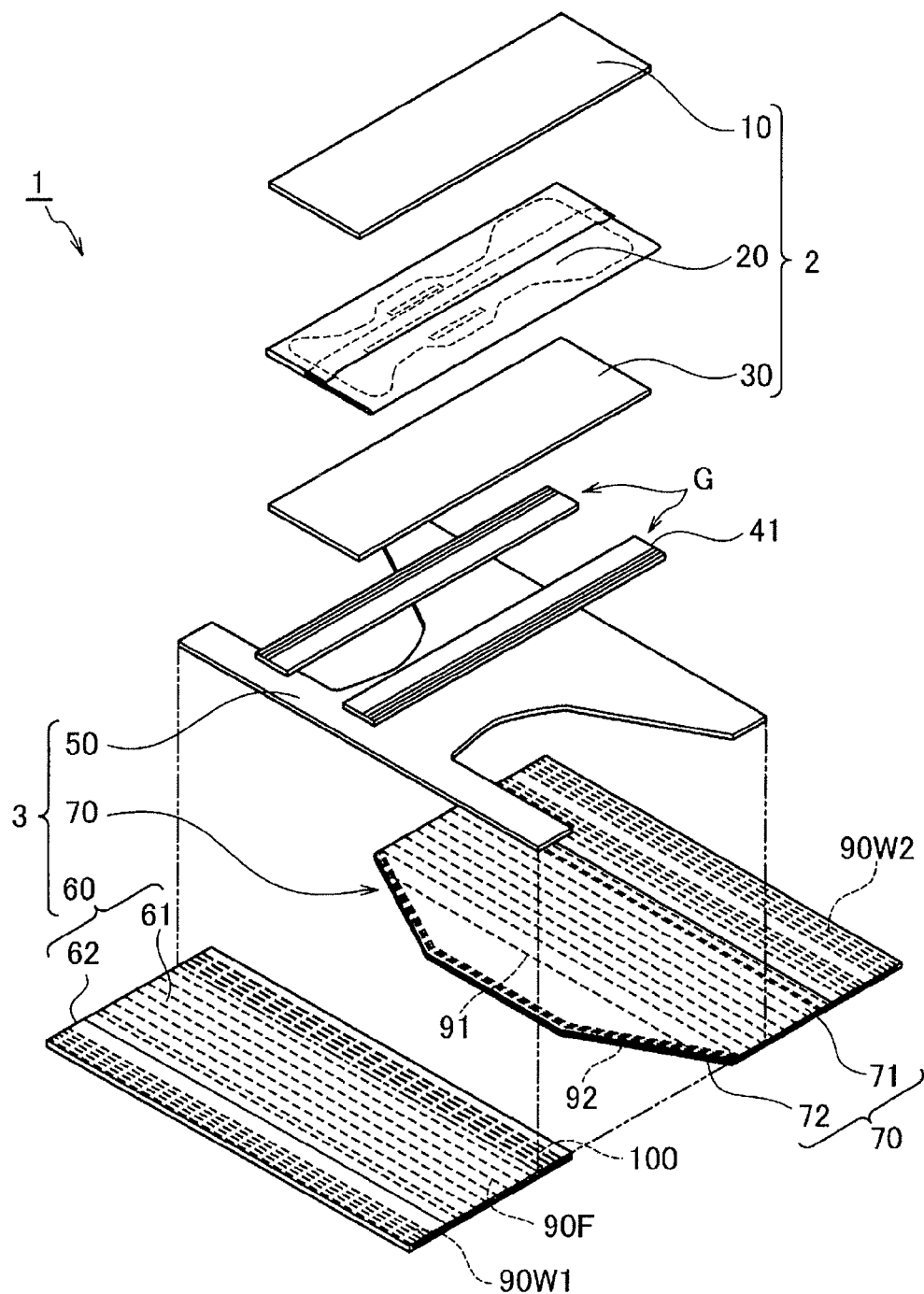
FIG. 1 is a developed view of an absorbent article according to a first embodiment of the present invention.

With reference to FIGS. 1 to 9, an absorbent article 1 according to a first embodiment of the present invention is explained. The absorbent article 1 according to the present invention is such as a pant-type diaper, absorbent underwear, or the like.

The absorbent article 1 according to the present embodiment has a chassis 3 and an absorber 2 both of which are in the same color. Herein, as long as the chassis 3 and the absorber 2 are given colors that are recognized as the same by average visual sensation of a wearer of the absorbent article 1, given colors are not required to have precisely equal values indicative of quantified colors (for example, luminance or the like).

For example, in the absorbent article 1 according to the present embodiment, the chassis 3 and the absorber 2 are given a white-based.

As shown in FIGS. 1 to 4, the absorber 2 is made up of a topsheet 10 on the absorber side, as a liquid-permeable sheet which comes in contact with the skin of a wearer; an absorber core 20; and a backsheet 30 on the absorber side, as a liquid-impermeable sheet.

As the topsheet 10 on the absorber side, such a material can be used, that is made from a hydrophilic nonwoven cloth made from a fiber such as polyolefin or polyethylene terephthalate (PET) and is manufactured by means of, e.g., spun bonding or air-through method. As the backsheet 30 on the absorber side, such a material can be used, that is made from a water-resistive film such as polyethylene (PE).

For example, the topsheet 10 on the absorber side is an air-through nonwoven cloth of 25 g/m$^2$ while the backsheet 30 on the absorber side is a moisture-permeable polyethylene film of 22 g/m$^2$.

Figure 3:
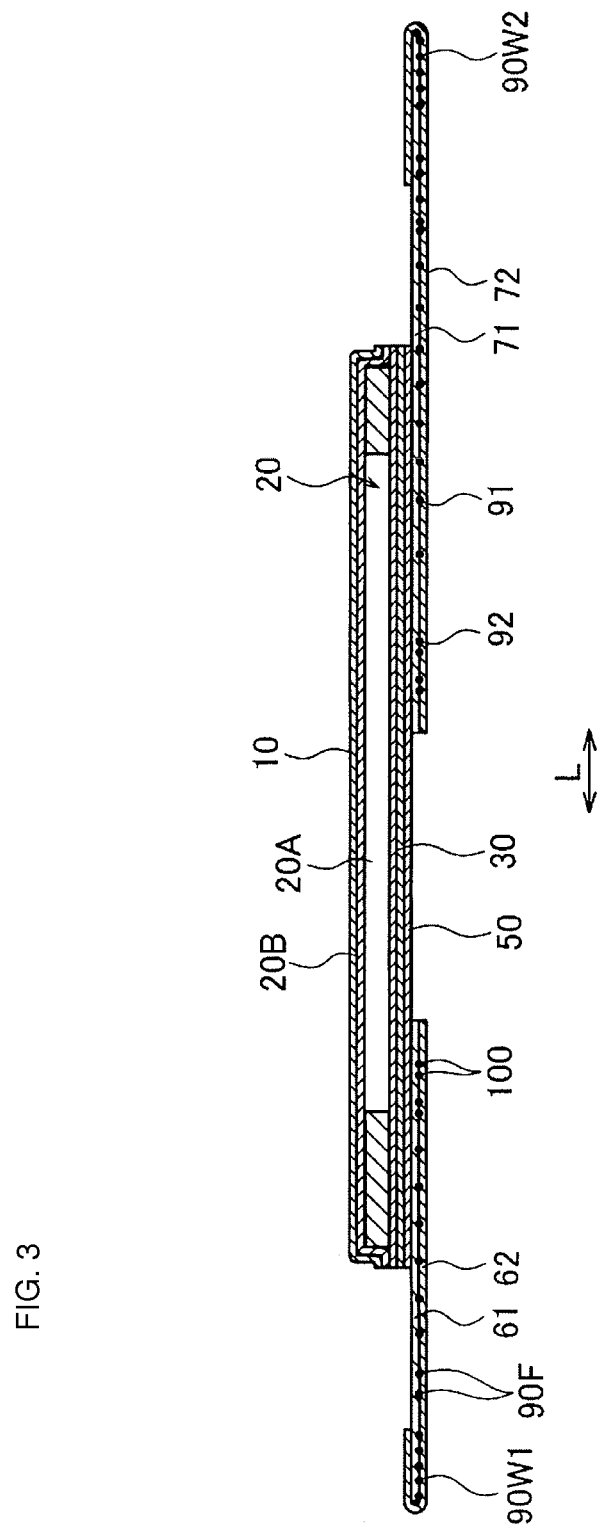
FIG. 3 is a cross-sectional view taken along the line A-A in a plan view of the absorbent article according to the first embodiment of the present invention.
Figure 4:
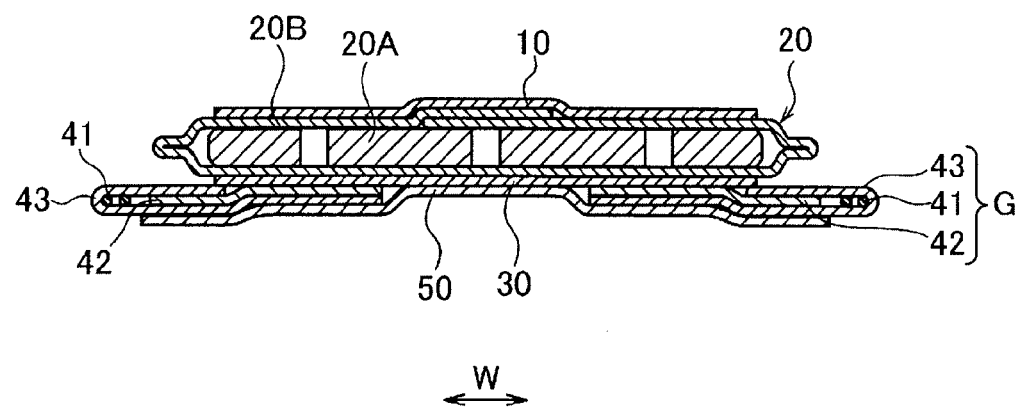
FIG. 4 is a cross-sectional view taken along the line B-B in a plan view of the absorbent article according to the first embodiment of the present invention.

As shown in FIGS. 3 and 4, the absorber core 20 is produced by packaging in a package sheet 20B, a mixture 20A of ground pulp (for example, 200 g/m$^2$), highly absorbent polymer (for example, 200 g/m$^2$), and the like.

As the package sheet 20B, such a material can be used, that is made from a hydrophilic nonwoven cloth made from a fiber such as polyolefin or polyethylene terephthalate and is manufactured by means of, e.g., spun bonding or air-through method. For example, the package sheet 20B is an SMS nonwoven cloth of 13 g/m$^2$.

The topsheet 10 on the absorber side, the backsheet 30 on the absorber side, and the package sheet 20B are joined to each other by means of a hot-melt adhesive (for example, spiral HMA).

For example, a basis weight of the hot-melt adhesive is within a range between 1.5 g/m$^2$ to 10 g/m$^2$. Further, as a joining method of the hot melt adhesive, other than spiral spray, methods such as slot coating, control seam, bead coating, curtain coater, and the like may be used.

Note that the absorber core 20 is a thin absorber having a thickness of about 2.0 mm, and its surface has little unevenness.

As shown in FIGS. 1 to 4, barrier cuffs G are provided on the both sides in a longitudinal direction L of the absorber 2. That is, the barrier cuffs G are joined to the both sides in a width direction W of the backsheet 30 on the absorber side.

Each of these barrier cuffs G is made up of thread-shaped elastic members 41 for the barrier cuff, a water-resistive film 42, and a hydrophobic nonwoven cloth 43.

As shown in FIG. 4, an end of the water-resistive film 42 and an end of the hydrophobic nonwoven cloth 43 substantially correspond to each other in terms of position in a rising fulcrum side of each of the barrier cuffs 30 (that is, the inner side in the width direction W), whereas the hydrophobic nonwoven cloth 43 is folded so as to sandwich the elastic members 41 for the barrier cuff in a free end of each of the barrier cuffs G (that is, an outer end in the width direction). Further, the water-resistive film 42 does not reach the free end of each of the barrier cuffs G.

As the hydrophobic nonwoven cloth 43, such a material can be used, that is made from a hydrophobic nonwoven cloth made from a fiber such as polyolefin or polyethylene terephthalate and is manufactured by means of, e.g., spun bonding. For example, the hydrophobic nonwoven cloth 43 is a hydrophobic SMS nonwoven cloth of 15 g/m$^2$.

Further, as the water-resistive film 42, a film made from polyethylene, polyethylene terephthalate, or the like can be used. For example, a moisture-permeable polyethylene film of 18 g/m$^2$ can be used.

The elastic members 41 for the barrier cuffs may be made from natural rubber, synthetic rubber, spandex, or the like. For example, the elastic members 41 for the barrier cuffs are made from spandex yarns of 620 tex, which are provided two by two on right and left sides. These elastic members 41 are fixed in a stretched state with an expansion magnification of 2.2 times, to the hydrophobic nonwoven cloth 43 by means of the hot-melt adhesive applied by a slit nozzle method.

Further, as shown in FIGS. 1 to 4, the chassis 3 is made up of a center sheet 50 and a front waistline sheet 60, and a rear waistline sheet 70.

Figure 2:
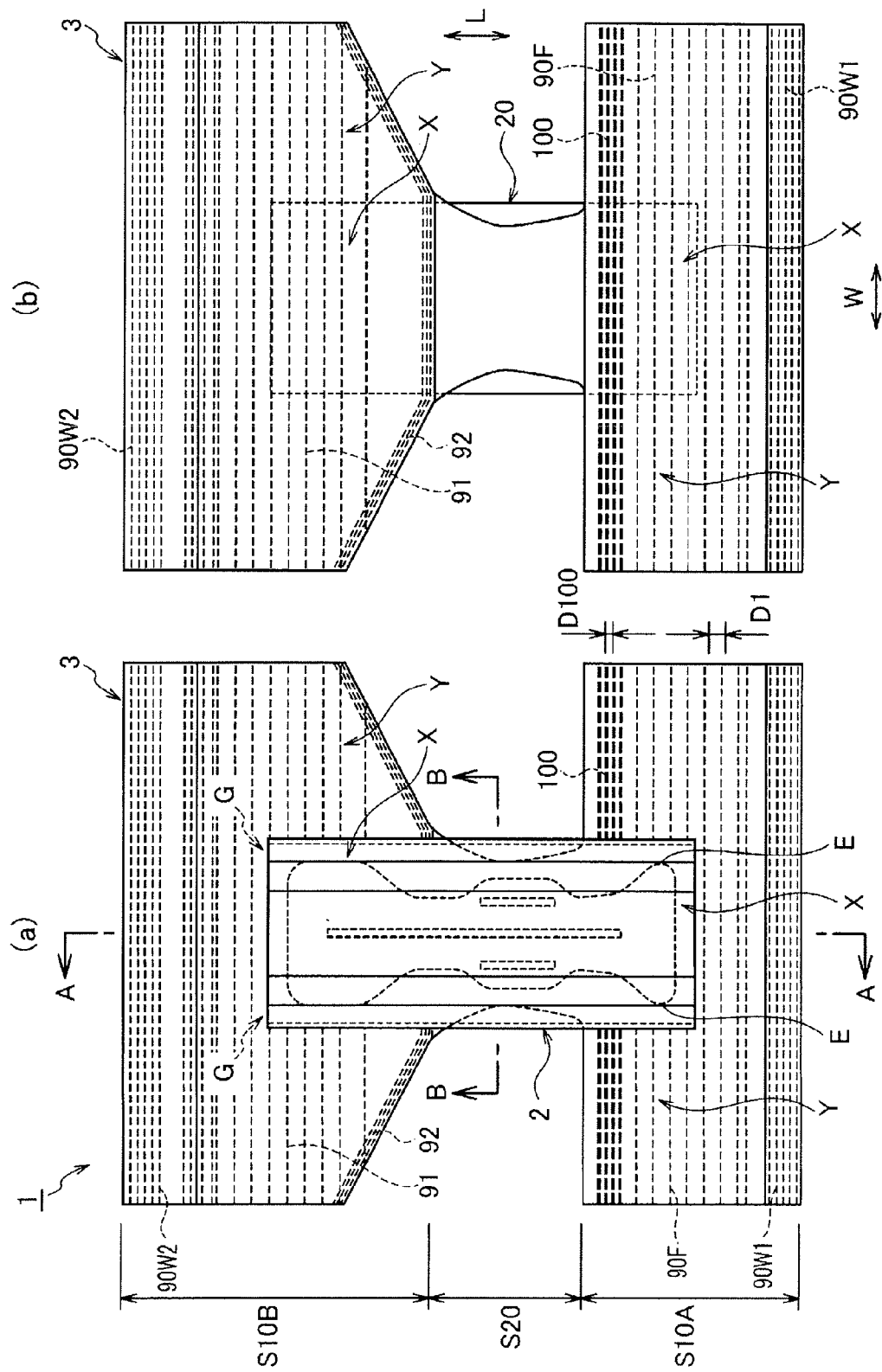
FIGS. 2(a) and 2(b) are plan views of the absorbent article according to the first embodiment of the present invention.

As a result, as shown in FIGS. 2(*a*) and 2(*b*), the chassis 3 has: a front waistline region S10A corresponding to the front waistline sheet 60; a rear waistline region S10B corresponding to the rear waistline sheet 70; and a crotch region S20 intervened between the front waistline region S10A and the rear waistline region S10B.

Herein, as shown in FIGS. 1 to 4, the absorber 2 is provided over the crotch region S20 to the front waistline region S10A and the rear waistline region S10B, on a skin contact surface side of the absorbent article 1, of the chassis 3.

Note that, as shown in FIGS. 2(*a*) and 2(*b*), in the front waistline region S10A and the rear waistline region S10B, the absorber 2 is provided in the central region in the width direction W.

The center sheet 50 is disposed on the skin contact surface side of the front waistline sheet 60 and the rear waistline sheet 70, and is made from, for example, the SMS nonwoven cloth of 15 g/m$^2$ which is made from polypropylene (PP).

Further, the front waistline sheet 60 is made from a front waistline topsheet 61 and a front waistline backsheet 62.

Herein, elastic members 90W1 for upper waistline gathers, elastic members 90F for front waistline gathers, and elastic members 100 for leg-hole gathers are retained in a stretched state between the front waistline topsheet 61 and the front waistline backsheet 62.

Further, as shown in FIG. 3, the front waistline backsheet 62 is folded toward the inner side in the longitudinal direction L at the end in the longitudinal direction L, and inside the folded part of the front waistline backsheet 62, the elastic members 90W1 for the upper waistline gathers are retained in a stretched state.

Similarly, the rear waistline sheet 70 is made up of a rear waistline topsheet 71 and a rear waistline backsheet 72.

Herein, elastic members 90W2 for the upper waistline gathers, elastic members 91 for the rear waistline gathers, elastic members 92 for the leg-hole gathers are retained in a stretched state between the rear waistline topsheet 71 and the rear waistline backsheet 72.

Further, as shown in FIG. 3, the rear waistline backsheet 72 is folded toward the inner side in the longitudinal direction L at the end in the longitudinal direction L, and inside the folded part of the rear waistline backsheet 72, the elastic members 90W2 for the upper waistline gathers are retained in a stretched state.

As the front waistline sheet 60 and the rear waistline sheet 70, such a material can be used, that is made from a hydrophobic nonwoven cloth such as polyolefin or polyethylene terephthalate, and is manufactured by means of, e.g., spun bonding or air-through method.

Further, it is preferable that the front waistline topsheet 61, the front waistline backsheet 62, the rear waistline topsheet 71, and the rear waistline backsheet 72 each have a basis weight within a range between 13 g/m² to 30 g/m².

For example, the front waistline topsheet 61 and the rear waistline topsheet 71 are an SMS nonwoven cloth of 15 g/m² made from polypropylene, whereas the front waistline backsheet 62 and the rear waistline backsheet 72 are a spun bond nonwoven cloth of 17 g/m² made from polypropylene.

Further, as the elastic members 90W1, 90W2 for the upper waistline gathers, the elastic members 90F for the front waistline gathers, and the elastic members 91 for the rear waistline gathers, natural rubber, synthetic rubber, spandex, or the like can be used, and their expansion magnification is preferably between 1.3 times and 4.0 times (in a case of spandex, a thickness is preferably between 300 dtex and 1300 dtex).

For example, an expansion magnification of the elastic members 90W1, 90W2 for the upper waistline gathers is 3.0 times (in a case of spandex, a thickness is 940 dtex), and an expansion magnification of the elastic members 90F for the front waistline gathers and the elastic members 91 for the rear waistline gathers is 2.5 times (in a case of spandex, a thickness is 780 dtex).

For example, the number of each of the elastic members 90W1, 90W2 for the upper waistline gathers is five, the number of the elastic members 90F for the front waistline gathers is eight, and the number of the elastic members 91 for the rear waistline gathers is eleven.

Further, in the rear waistline topsheet 71 and the rear waistline backsheet 72, the elastic members 92 for the leg-hole gathers are disposed so as to reach from one end to the other end in the width direction W while curving along the inner end in the longitudinal direction L (a region forming a leg-hole opening). For example, an expansion magnification of the elastic members 92 for the leg-hole gathers is 1.8 times (in a case of spandex, a thickness if 780 dtex).

Further, in the front waistline topsheet 61 and the front waistline backsheet 62, the elastic members 100 for the leg-hole gathers are disposed linearly between one end and the other end in the width direction W. For example, an expansion magnification of the elastic members 100 for the leg-hole gathers is 2.0 times (in a case of spandex, a thickness is 780 dtex), and the number of the elastic members 100 for the leg-hole gathers is four.

Note that, as shown in FIGS. 1 to 4, respective members making up the center sheet 50, the front waistline sheet 60, and the rear waistline sheet 70 described above are configured so as to be joined together by means of a heat seal, sonic seal, hot-melt adhesive, or the like.

Further, the front waistline topsheet 61 and the front waistline backsheet 62 are joined together by means of hot-melt adhesive which is directly applied to the elastic members 90F for the front waistline gathers and the elastic members 100 for the leg-hole gathers. The rear waistline topsheet 71 and the rear waistline backsheet 72 are joined together by means of hot-melt adhesive which is directly applied to the elastic members 91 for the rear waistline gathers.

That is, in the absorbent article 1 according to the present embodiment, the hot-melt adhesive is not applied to the front waistline topsheet 61 and the front waistline backsheet 62. With such a configuration, the front waistline topsheet 61 and the front waistline backsheet 62 can be improved in softness.

Further, the hot-melt adhesive is not applied to the rear waistline topsheet 71 and the rear waistline backsheet 72 within a region to which the elastic members 91 for the rear waistline gathers are joined. With such a configuration, the rear waistline topsheet 71 and the rear waistline backsheet 72 in this region can be improved in softness.

On the other hand, the hot-melt adhesive may be applied by spiral spray to the rear waistline backsheet 72 within a region to which the elastic members 92 for the leg-hole gathers are joined, along a pattern of the elastic members 92 for the leg-hole gathers.

Note that the hot-melt adhesive may be partially applied by an application means such as spiral spray, or control seam, to a part where the above-described elastic members are spaced at an interval of 10 mm or more.

Used as such a hot-melt adhesive is, for example, rubber series such as styrene-isoprene-styrene (SIS), polystyrene-butadiene-styrene (SBS), or styrene-ethylene-butylene-styrene (SEBS), or olefin series.

As described above, in the absorbent article 1 according to the present embodiment, in the front waistline region S10A and the rear waistline region S10B, the plurality of waistline elastic members are provided along the width direction W of the absorbent article 1.

Specifically, in the front waistline region S10A, the plurality of elastic members 90W1 for the upper waistline gathers, the plurality of elastic members 90F for the front waistline gathers, and the plurality of elastic members 100 for the leg-hole gathers are provided along the width direction W of the absorbent article 1.

Further, in the rear waistline region S10B, along the width direction W of the absorbent article 1, the plurality of elastic members 90W2 for the upper waistline gathers, the plurality of elastic members 91 for the rear waistline gathers, the plurality of elastic members 92 for the leg-hole gathers, and the like are provided.

Herein, in the absorbent article 1 according to the present embodiment, within the crotch region S20, the waistline elastic members provided in the front waistline region S10A (for example, the elastic members 90F for the front waistline gathers and the elastic members 100 for the leg-hole gathers) and the waistline elastic members provided in the rear waistline region S10B (for example, the elastic members 91 for the rear waistline gathers and the elastic members 92 for the leg-hole gathers) are disposed so as not to come in contact with each other.

Further, in the absorbent article 1 according to the present embodiment, as shown in FIGS. 2(a) and 2(b), in the front waistline region S10A or the rear waistline region S10B, an identifier of linear shape is provided so as to be visually recognizable from only the non-skin contact surface side of the absorbent article 1, in a first region X which is provided with the absorber 2, and to be visually recognizable from both the non-skin contact surface side and the skin contact surface side of the absorbent article 1, in a second region Y which is not provided with the absorber 2.

For example, such an identifier is made up of, out of the plurality of waistline elastic members, waistline elastic members which are provided closer to the non-skin contact surface of the absorbent article 1 than the absorber 2, over the first region X and the second region Y.

In the absorbent article 1 according to the present embodiment, a white-based color is given to the elastic members 90W1, 90W2 for the upper waistline gathers, the elastic member 90F for the front waistline gathers, the elastic members 91 for the rear waistline gathers, and the elastic members 92 for the leg-hole gathers, whereas a blue-based color is given to the elastic members 100 for the leg-hole gathers.

That is, in the absorbent article 1 according to the present embodiment, the elastic members 100 for the leg-hole gathers make up the aforementioned identifier.

Further, the waistline elastic members which make up the identifier may be arranged so as to have a shorter interval (insertion pitch) than an interval (insertion pitch) between the waistline elastic members which do not make up the identifier.

In this regard, in the absorbent article 1 according to the present embodiment, an insertion pitch D100 of the elastic members 100 for the leg-hole gathers which make up the identifier is 5 mm, whereas an insertion pitch Dl of the elastic members 90F for the front waistline gathers which do not make up the identifier is 15 mm.

Further, likewise the configuration described above, by making the interval (insertion pitch) between the elastic members 100 for the leg-hole gathers shorter than the interval (insertion pitch) between the elastic members 90F for the front waistline gathers, the elastic members 100 for the leg-hole gathers can be made to stand out as compared with the elastic members 90F for the front waistline gathers.

The waistline elastic members which make up the identifier may be configured so as to be thicker than the waistline elastic members which do not make up the identifier.

Likewise the configuration described above, by making the elastic members 100 for the leg-hole gathers thicker than the elastic members 90F for the front waistline gathers, the elastic members 100 for the leg-hole gathers can be made to stand out as compared with the elastic members 90F for the front waistline gathers.

Figure 5:
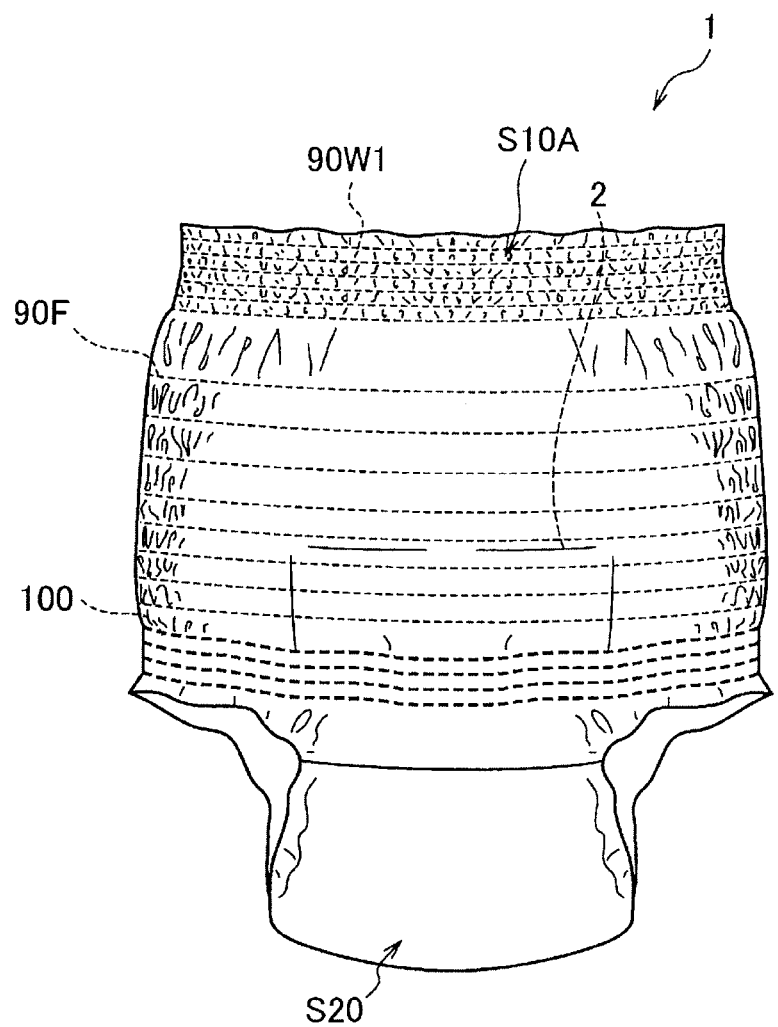
FIG. 5 is an external view when a surface of the absorbent article according to the first embodiment of the present invention is viewed from the front side.
Figure 6:
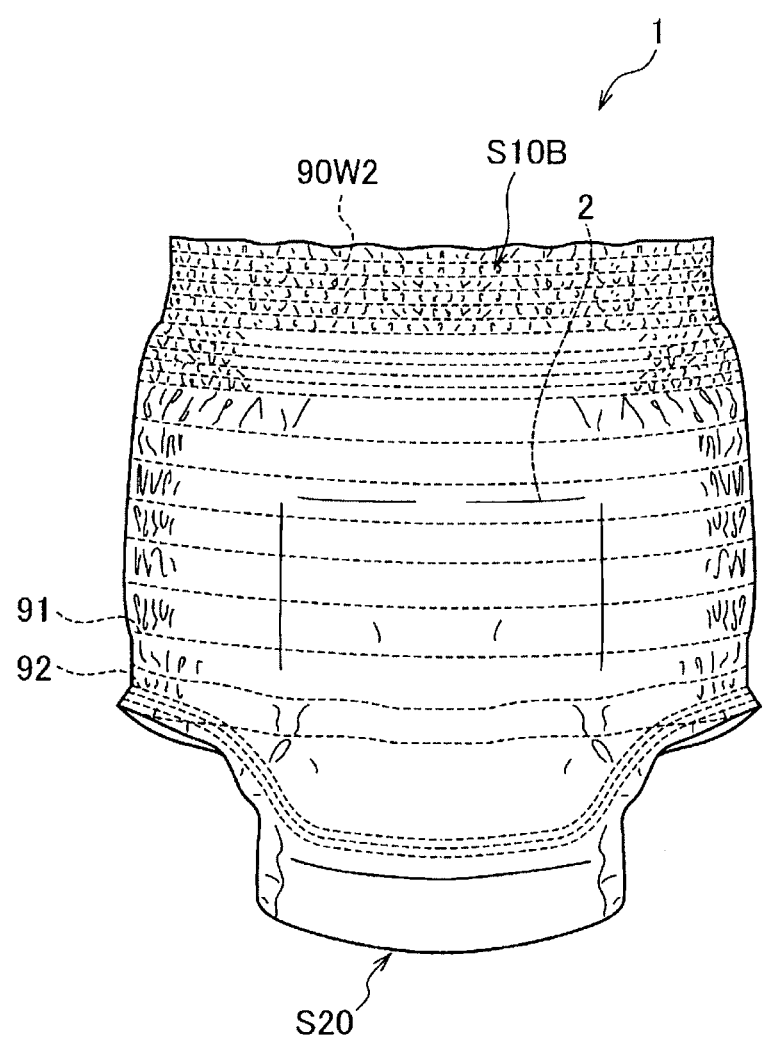
FIG. 6 is an external view when the surface of the absorbent article according to the first embodiment of the present invention is viewed from the rear side.
Figure 7:
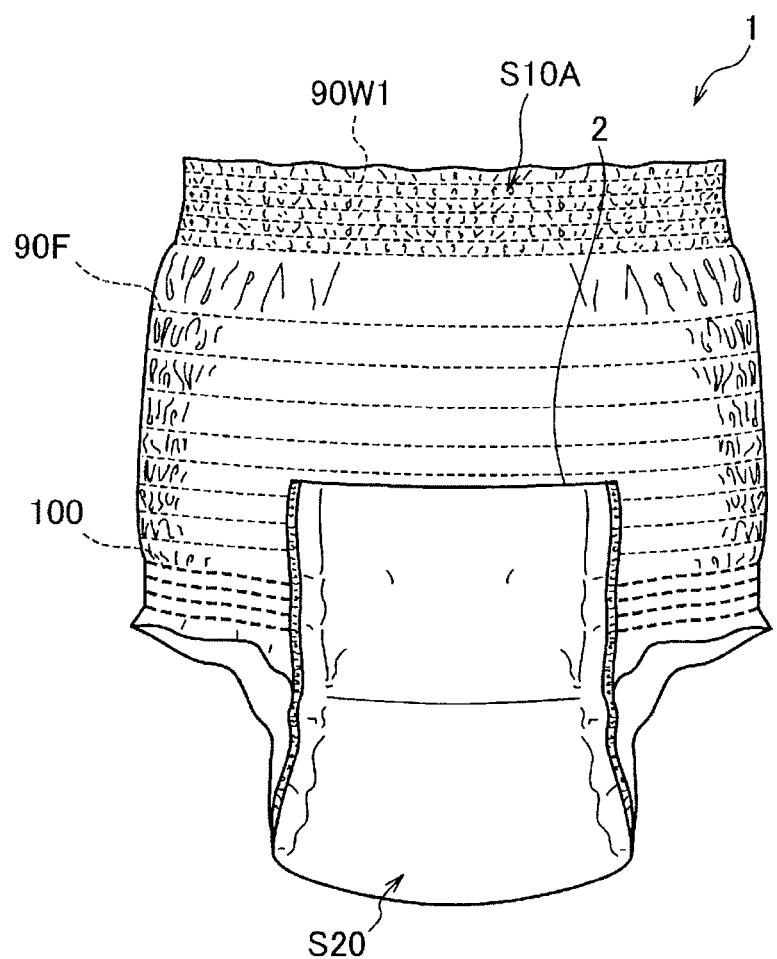
FIG. 7 is an external view when a reverse surface of the absorbent article according to the first embodiment of the present invention is viewed from the front side.
Figure 8:
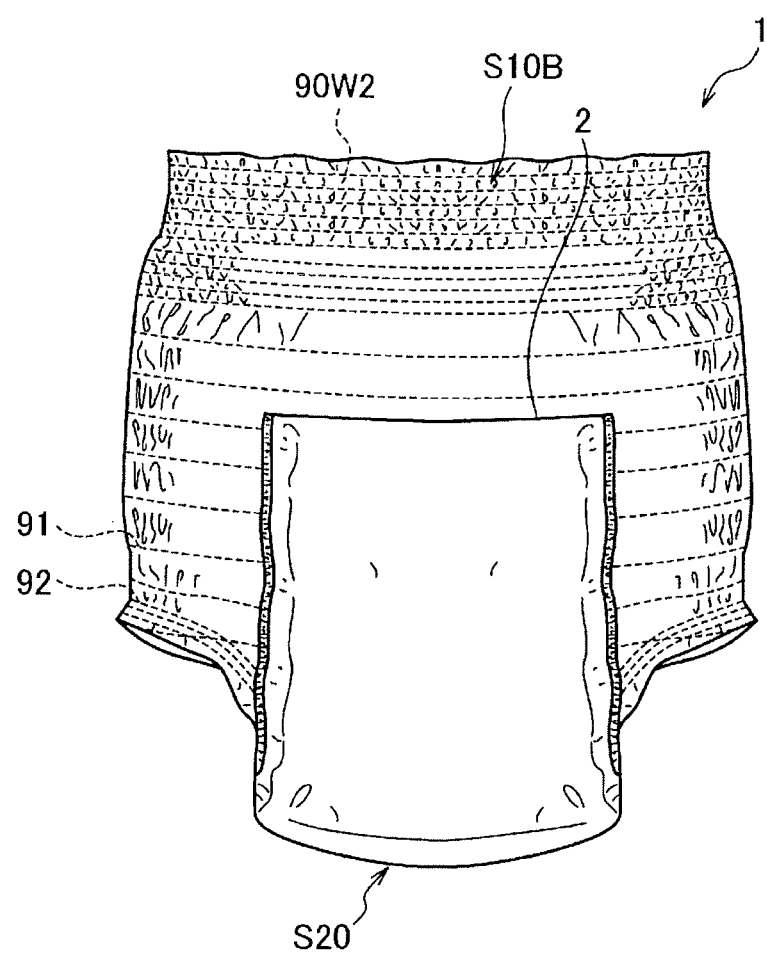
FIG. 8 is an external view when the reverse surface of the absorbent article according to the first embodiment of the present invention is viewed from the rear side.

FIG. 5 is an external view when the surface of the absorbent article 1 according to the present embodiment is viewed from the front side. FIG. 6 is an external view when the surface of the absorbent article 1 according to the present embodiment is viewed from the rear side. FIG. 7 is an external view when the reverse surface of the absorbent article 1 according to the present embodiment is viewed from the front side. FIG. 8 is an external view when the reverse surface of the absorbent article 1 according to the present embodiment is viewed from the rear side.

As shown in FIG. 5, with the absorbent article 1 in a normal state where it is not worn inside out, the wearer can visually recognize the elastic members 100 for the leg-hole gathers which is given a different color from the chassis 3, in both the first region X and the second region Y.

On the other hand, as shown in FIG. 7, with the absorbent article 1 turned inside out, the wearer cannot visually recognize part of the elastic members 100 for the leg-hole gathers, that is, the wearer cannot visually recognize the elastic members 100 for the leg-hole gathers in the first region X.

Therefore, the wearer can easily discriminate whether or not the absorbent article 1 is turned inside out, by visually recognizing the elastic members 100 for the leg-hole gathers in the first region X.

Further, as shown in FIGS. 5 and 6, the wearer can visually recognize the elastic members 100 for the leg-hole gathers which is given a different color from the chassis, by viewing the surface of the absorbent article 1 from the front side. However, the elastic members 100 for the leg-hole gathers cannot be visually recognized by viewing the surface of the absorbent article 1 from the rear side.

Therefore, the wearer can easily discriminate between the front side and the rear side of the absorbent article 1, by visually recognizing the elastic members 100 for the leg-hole gathers.

Hereinafter, with reference to FIG. 9, part of a manufacturing method of the absorbent article 1 according to the present embodiment is explained. As far as the other method that is not explained, the existing method can be used.

Figure 9:
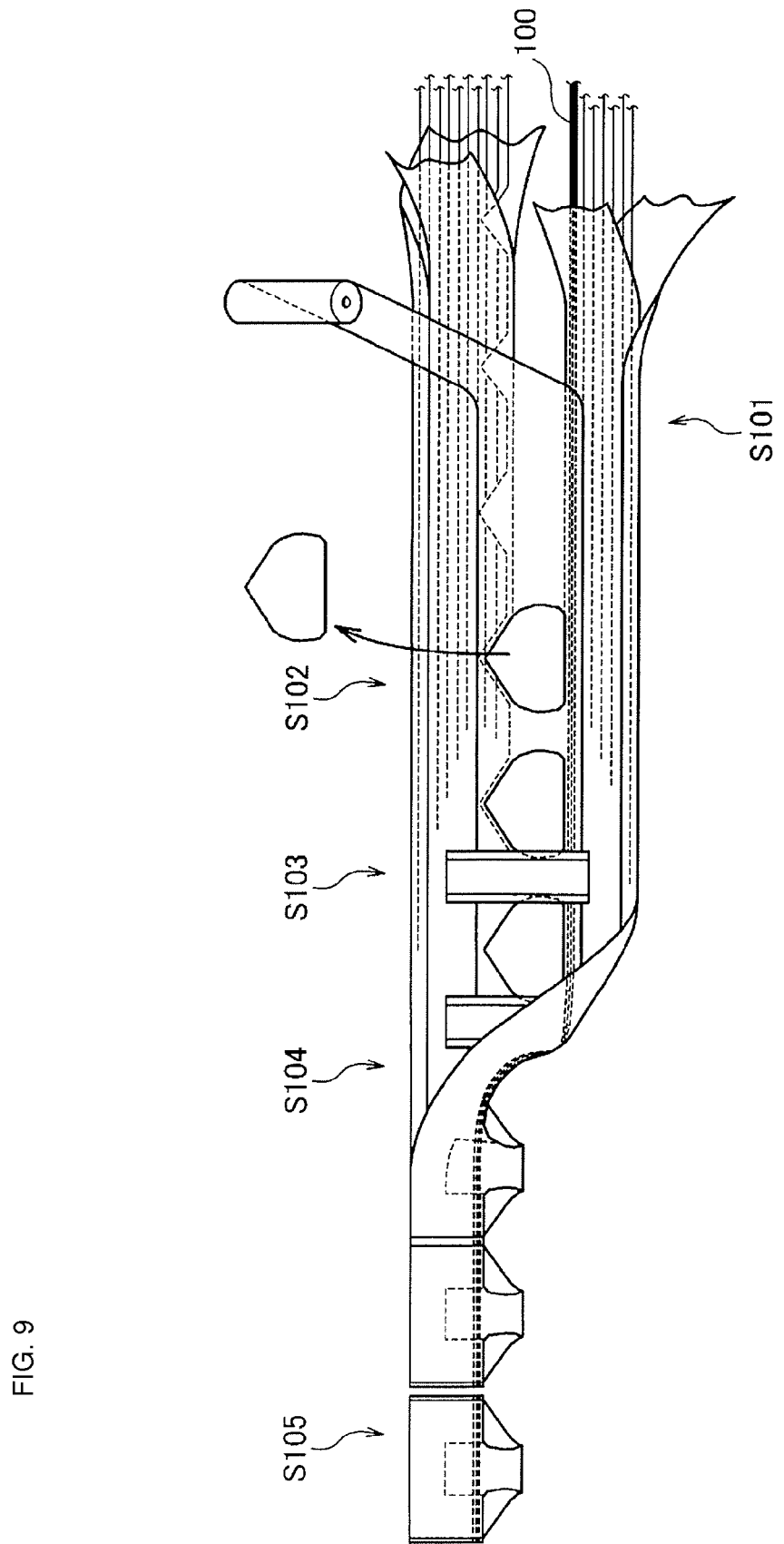
FIG. 9 is a view for illustrating a manufacturing method of the absorbent article according to the first embodiment of the present invention.

As shown in FIG. 9, the chassis 3 is produced in step S101. Herein, used as the elastic members 100 for the leg-hole gathers, which are to be inserted, are those which are given a different color form the chassis 3 and the absorber 2.

In step S102, the leg-hole opening is formed by cutting at once the center sheet 50, the front waistline sheet 60, and the rear waistline sheet 70 into a predetermined shape.

In step S103, the absorber 2 is arranged between the leg-hole openings formed in step S102.

In step S104, after the front waistline sheet 60 is folded toward the rear waistline sheet 70, the front waistline sheet 60 and the rear waistline sheet 70 are jointed together.

In step S105, the absorbent article 1 is produced by cutting the joining region between the front waistline sheet 60 and the rear waistline sheet 70.

With the absorbent article 1 according to the present embodiment, the elastic members 100 for the leg-hole gathers are given a different color (for example, a blue-based color) from a color (for example, a white-based color) of the chassis 3 (including the elastic members 90F for the front waistline gathers) and the absorber 2, thereby being able to make the elastic members 100 for the leg-hole gathers stand out. Thus, in a case where the wearer can visually recognize the elastic members 100 for the leg-hole gathers in the first region X, he or she can notice the fact he or she is viewing the front face of the absorbent article 1 in a normal state where it is not turned inside out.

Herein, with the absorbent article 1 according to the present embodiment, since it is configured so that the elastic members 100 for the leg-hole gathers, which are required for the absorbent article 1 to function properly, are used as an identifier, the absorbent article 1 can be manufactured without use of any members which are not required for the absorbent article 1 to function properly.

First Modification

Figure 10:
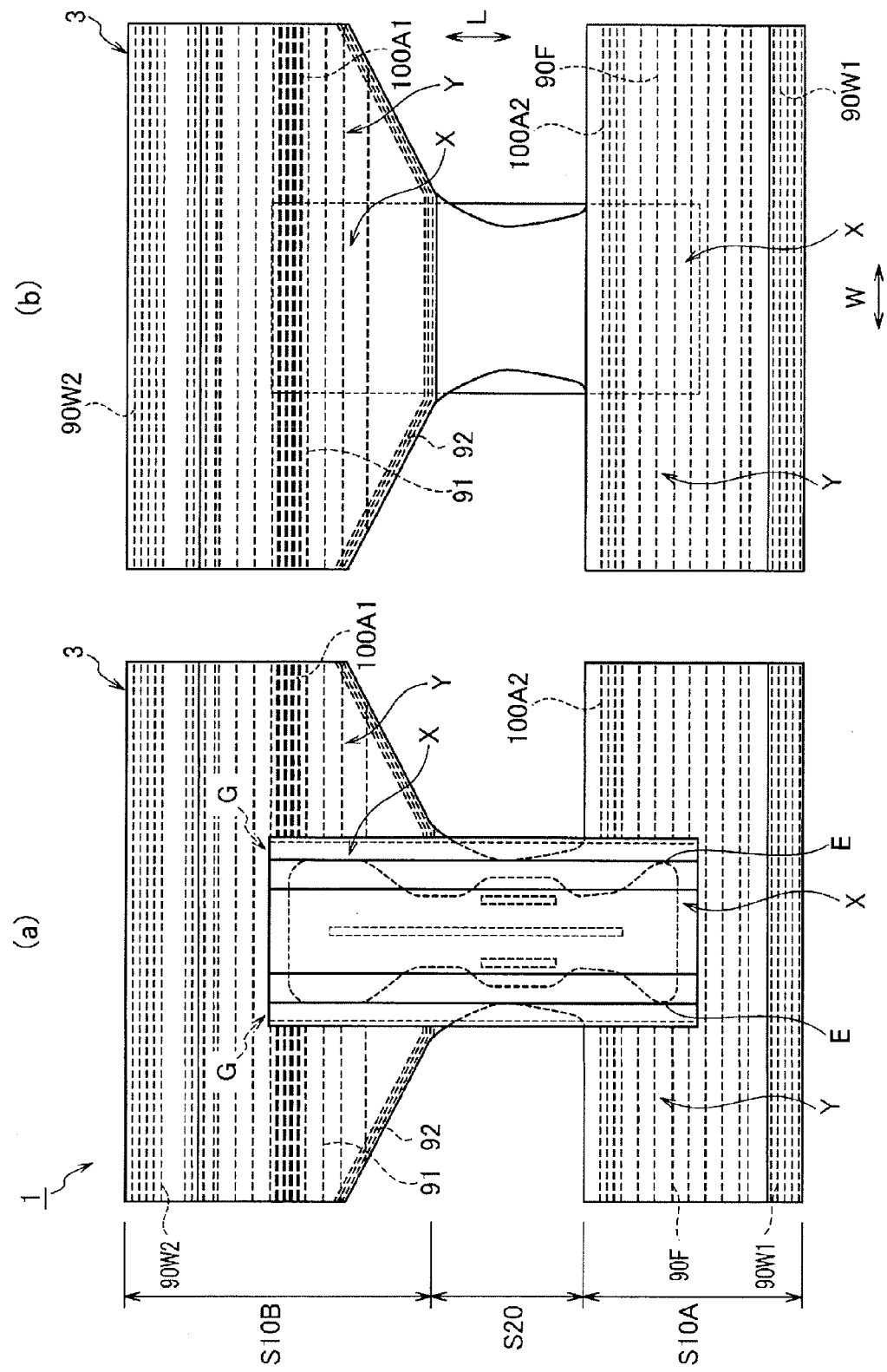
FIGS. 10(*a*) and 10(*b*) are plan views of an absorbent article according to a first modification of the present invention.

With reference to FIGS. 10(a) and 10(b), an absorbent article 1 according to a first modification of the present invention is explained. Hereinafter, an absorbent article 1 according to this first modification is explained with a focus on differences from the absorbent article 1 according to the first embodiment described above.

As shown in FIGS. 10(a) and 10(b), the identifier described above is made up of elastic members 100A1 for the rear waistline gathers provided in the rear waistline region S10B, instead of elastic members 100A2 for the leg-hole gathers provided in the front waistline region S10A.

In the absorbent article 1 according to this first modification, the elastic members 100A1 for the rear waistline gathers making up the identifier are given a different color (for example, a blue-based color) from a color (for example, a white-based color) given to the chassis 3 (including the elastic members 91 for the rear waistline gathers) and the absorber 2.

That is, in the absorbent article 1 according to this first modification, the waistline region S10B is provided with the elastic members 91, 100A for the rear waistline gathers in a different color.

Further, in the absorbent article 1 according to this first modification, the elastic members 100A1 for the rear waistline gathers are arranged so as to have a shorter interval (insertion pitch) than an interval (insertion pitch) between the elastic members 91 for the rear waistline gathers.

Yet further, in the absorbent article 1 according to this first modification, the elastic members 100A1 for the rear waistline gathers are configured so as to be thicker than the elastic members 91 for the rear waistline gathers.

Note that, in the absorbent article 1 according to this first modification, the aforementioned identifier may be made up of the elastic members 92 for the leg-hole gathers arranged along the region which forms the leg-hole opening, instead of the elastic members 100A1 for the rear waistline gathers provided in the rear waistline region S10B.

Second Modification

Figure 11:
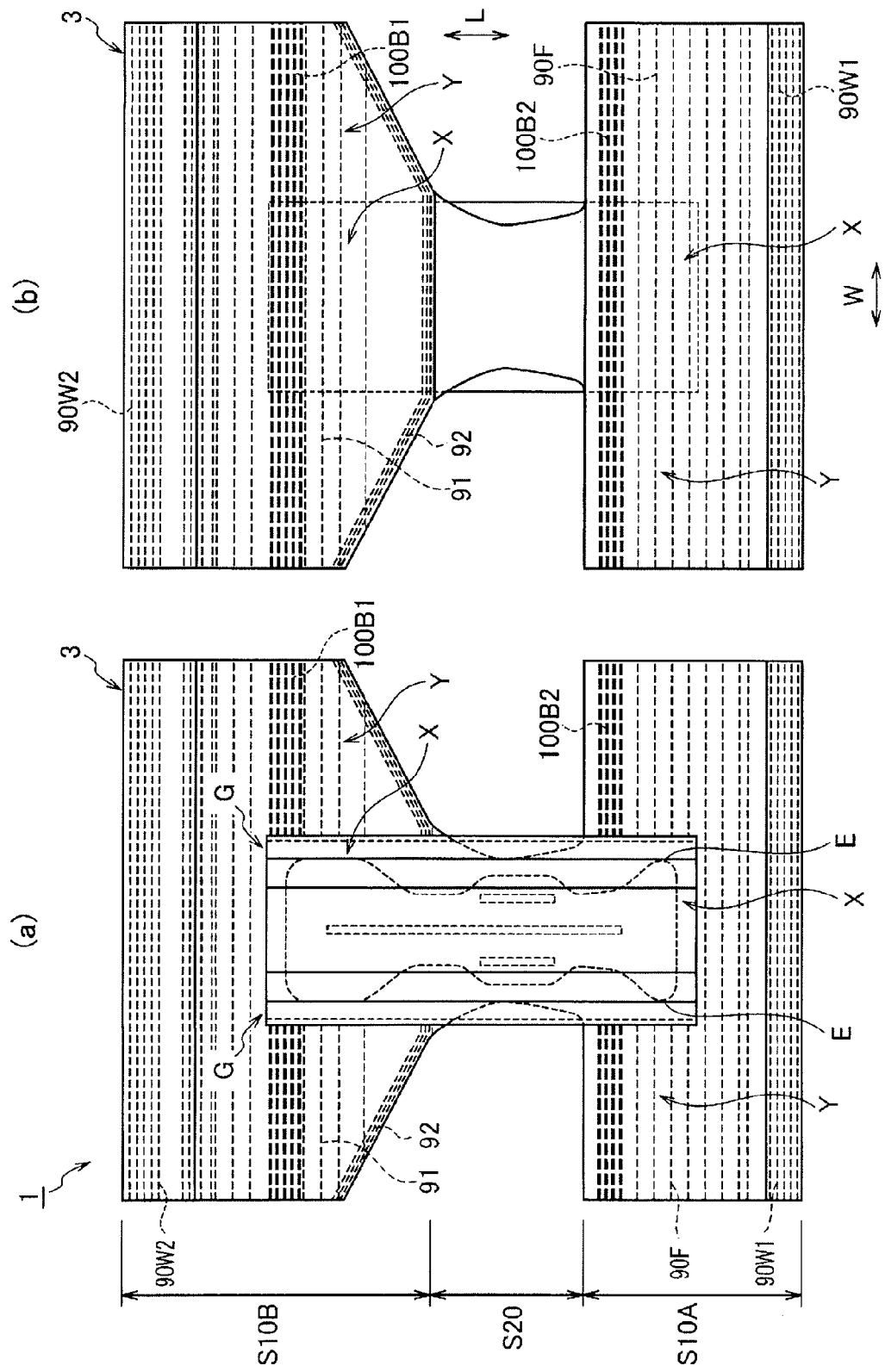
FIGS. 11(*a*) and 11(*b*) are plan views of an absorbent article according to a second modification of the present invention.

With reference to FIGS. 11(a) and 11(b), an absorbent article 1 according to a second modification of the present invention is explained. Hereinafter, an absorbent article 1 according to this second modification is explained with a focus on differences from the absorbent article 1 according to the first embodiment described above.

In the absorbent articles 1 according to the first embodiment and the first modification, the identifier described above is provided in either one of the front waistline region S10 and the rear waistline region S10B, whereas in the absorbent article 1 according to this second modification, as shown in FIGS. 11(a) and 11(b), such an identifier is provided in each of the front waistline region S10A and the rear waistline region S0B.

Third Modification

Note that the above-described identifier may be formed by making color print on the front waistline sheet 60, the rear waistline sheet 70, and the like.

Further, a configuration of the chassis 3 and the absorber 2 may be different from a configuration of those in the above-described absorbent article 1 according to the first embodiment.

Figure 12:
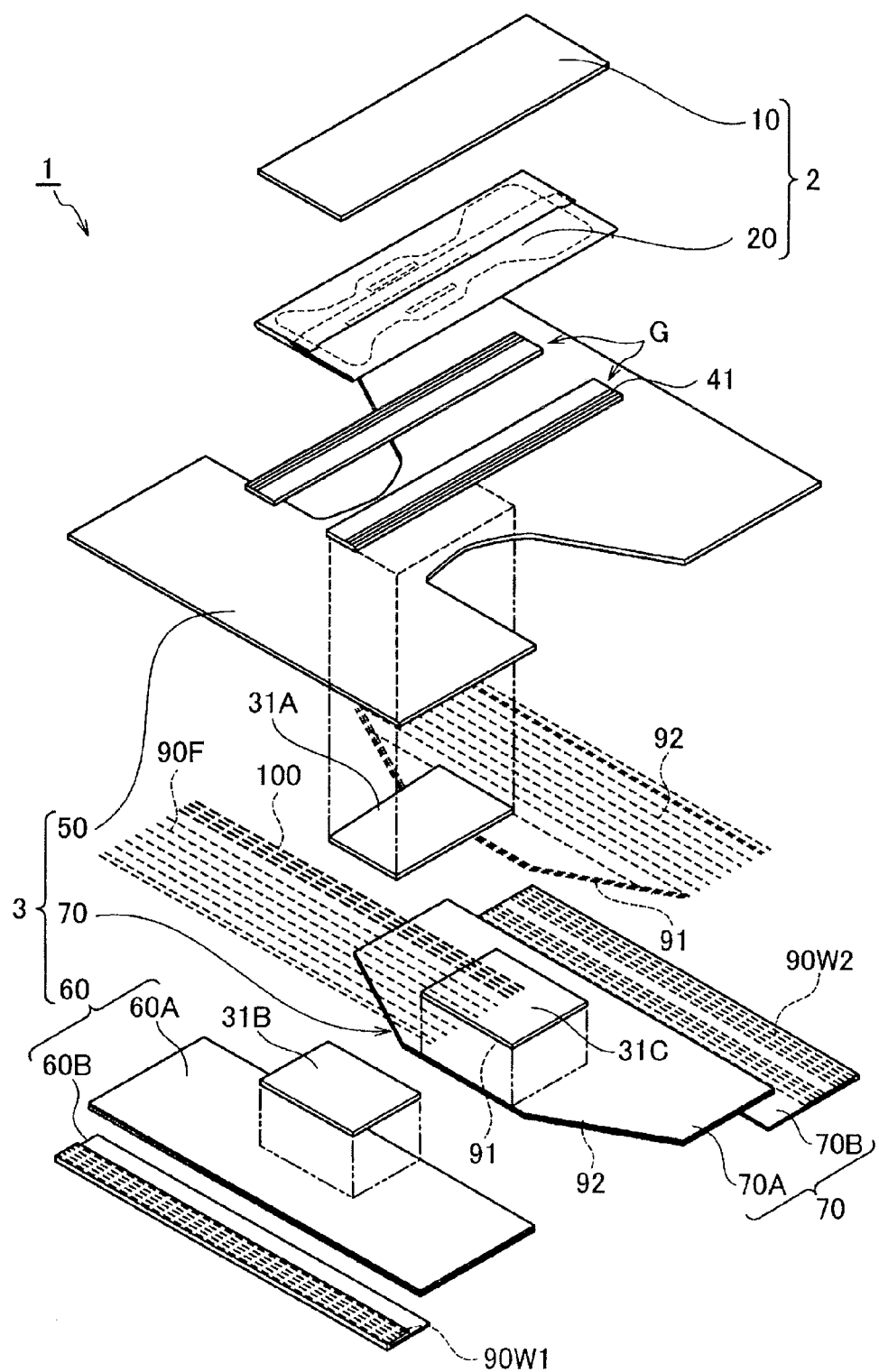
FIG. 12 is a developed view of an absorbent article according to a third modification of the present invention.

For example, as shown in FIG. 12, as a barrier film, which is to be provided on the non-skin contact surface side of the absorbent article 1, of the absorber core 20, barrier films 31A to 31C may be provided on the chassis 3 side, instead of the backsheet 30 on the absorber side which is provided inside the absorber 2 in the absorbent article 1 according to the first embodiment.

Note that, in an example shown in FIG. 12, the front waistline sheet 60 is made up of sheets 60A, 60B, whereas the rear waistline sheet 70 is made up of sheets 70A, 70B.

In the absorbent article 1 with such a configuration, the absorber 2 is made up of the absorber core 20 and the topsheet 10 on the absorber side.

Further, the chassis 3 and the absorber 2 may be formed as a united body. In the absorbent article 1 with such a configuration, the absorber 2 is made up of the absorber core 20. That is, the absorber 1 does not include the topsheet 10 on the absorber side and the backsheet 30 on the absorber side.

As described above, the present invention has been described in detail by using the above-described embodiment. However, it is apparent to those skilled in the art that the present invention is not limited to the embodiment described in this description. The present invention can be modified and changed without departing from the gist and the scope of the present invention defined by the appended claims. Therefore, the description is aimed at illustration and explanation of the present invention, and does not have any meaning which limits the present invention.

The entire contents of Japanese Patent Application No. 2010-088917 (filed on Apr. 7, 2010) are incorporated in the present specification by reference.

INDUSTRIAL APPLICABILITY

As described above, according to the present invention, it is possible to provide an absorbent article by which a wearer can easily discriminate between the front side and the rear side.

REFERENCE SIGNS LIST

1 . . . Absorbent article
S10A . . . Front waistline region
S10B . . . rear waistline region
S20 . . . Crotch region
X . . . First region
Y . . . Second region
2 . . . Absorber
3 . . . Chassis
90W1, 90W2 . . . Elastic members for upper waistline gathers
90F . . . Elastic members for front waistline gathers
91 . . . Elastic members for rear waistline gathers
92, 100, 100A2, 100B2 . . . Elastic members for leg-hole gathers

The invention claimed is:
1. An absorbent article comprising:
a chassis; and
an absorber having a same color as the chassis,
wherein
the chassis has a front region, a rear region, and a crotch region intervened between the front region and the rear region,
the absorber is provided closer to a skin contact surface side of the absorbent article than the chassis, and extends over the crotch region to the front region and the rear region,
in the front region and the rear region,
a plurality of front and rear elastic members is provided in a width direction of the absorbent article, and
a plurality of front and rear leg hole elastic members is provided along leg holes of the absorbent article,
in the crotch region, the front leg hole elastic members provided in the front region and the rear leg hole elastic members provided in the rear region are arranged so as not to come in contact with each other,
in the front and rear regions, an identifier is provided so as to be visually recognizable from only a non-skin contact surface side of the absorbent article, in a first region which is provided with the absorber, and to be visually recognizable from both the non-skin contact surface side and the skin contact surface side of the absorbent article, in a second region which is not provided with the absorber, the identifier is arranged over the first region and the second region, the front and rear leg hole elastic members overlap the absorber in a thickness of the absorbent article and define the identifier, the front leg hole elastic members arranged in the front region linearly extend along the leg holes from a lateral edge of the front region to an opposing lateral edge of the front region, and the rear leg hole elastic members arranged in the rear region are curves extending along the leg hole from a lateral edge of the rear region to an opposing lateral edge of the rear region.

2. The absorbent article according to claim 1, wherein the front and rear leg hole elastic members are provided closer to the non-skin surface side of the absorbent article than the absorber, and over the first region and the second region.

3. The absorbent article according to claim 1, wherein the front and rear leg hole elastic members which make up the identifier are arranged at a shorter interval than an interval between the front and rear elastic members which do not make up the identifier.

4. The absorbent article according to claim 1, wherein the front and rear leg hole elastic members which make up the identifier are thicker than the front and rear elastic members which do not make up the identifier.

5. The absorbent article according to claim 1, wherein the identifier is further defined by the front and rear elastic members which overlap the absorber.

6. The absorbent article according to claim 5, wherein the front elastic members, which define the identifier, extend linearly from the lateral edge of the front region to the opposing lateral edge of the front region, and the rear elastic members, which define the identifier, extend linearly from the lateral edge of the rear region to the opposing lateral edge of the rear region.

* * * * *